US009933818B2

(12) United States Patent
Vacas Jacques

(10) Patent No.: US 9,933,818 B2
(45) Date of Patent: Apr. 3, 2018

(54) TEXTILE MOTHERBOARD, HAVING A MODULAR AND INTERCHANGEABLE DESIGN, FOR MONITORING, REPORTING AND CONTROLLING

(71) Applicant: Paulino Vacas Jacques, Guanajuato (MX)

(72) Inventor: Paulino Vacas Jacques, Guanajuato (MX)

( * ) Notice: Subject to any disclaimer, the term of this patent is extended or adjusted under 35 U.S.C. 154(b) by 0 days.

(21) Appl. No.: 15/124,710

(22) PCT Filed: Jul. 14, 2014

(86) PCT No.: PCT/MX2014/000104
§ 371 (c)(1),
(2) Date: Sep. 9, 2016

(87) PCT Pub. No.: WO2015/137794
PCT Pub. Date: Sep. 17, 2015

(65) Prior Publication Data
US 2017/0017264 A1    Jan. 19, 2017

(30) Foreign Application Priority Data

Mar. 10, 2014  (MX) .................... MX/a/2014/002826

(51) Int. Cl.
*G06F 1/16* (2006.01)
*A41B 1/08* (2006.01)
(Continued)

(52) U.S. Cl.
CPC ................ *G06F 1/163* (2013.01); *A41B 1/08* (2013.01); *A41D 1/005* (2013.01); *A61B 5/6805* (2013.01);
(Continued)

(58) Field of Classification Search
CPC ........ H05K 1/038; H05K 1/165; H05K 1/283; H05K 3/10
(Continued)

(56) References Cited

U.S. PATENT DOCUMENTS 5,824,996 A * 10/1998 Kochman .......... A41D 13/0051
                                                        219/529
6,210,771 B1 * 4/2001 Post ....................... D03D 15/00
                                                        139/1 R
(Continued)

FOREIGN PATENT DOCUMENTS

KR    20130081765 A    7/2013
TW      201320310 A    5/2013

OTHER PUBLICATIONS

International Search Report issued in connection with the corresponding International Application No. PCT/MX2014/000104.
(Continued)

*Primary Examiner* — Xiaoliang Chen
(74) *Attorney, Agent, or Firm* — The H.T. Than Law Group

(57) ABSTRACT

The present invention concerns a textile motherboard (TMB) employable in garments, tablecloths, gowns, etc. that incorporates at least a central processing unit (CPU) or a peripheral or a combination thereof, with the intention of monitoring, informing, or controlling parameters of interest. The garments may be utilized or worn by users (human or not). The textile of the garment is utilized as substrate to conform the TMB. The TMB may exhibit multiple-layer structures and VIAs (Vertical Interconnect Accesses). The routings of the TMB are conformed of textile material capable of transmitting signals between CPU and a means to register information or between the CPU and the combination of peripherals. Layers, routings, and VIAs may be incorporated into the TMB by using known textile manipu-
(Continued)

lation techniques such as: knitting, weaving, stamping, perforating, or they may also be printed on the textiles. Every component is modular and interchangeable and connects to the TMB utilizing textile connectors such as snaps, hooks, or similar elements. TMB, CPU, and peripherals are washable. CPU and peripherals may be mounted on textile boards, as well as on rigid or flexible PCBs (printed circuit boards), utilizing discrete electronic and photonic elements. The CPU includes a microcontroller, a microprocessor, or a comparable element. The peripherals include photonic transducers or electronic transducers or combinations thereof such as: capacitive, pulse, humidity, temperature, accelerometers, and gyroscopes sensors. The peripherals also include screens, modules for serial communications, radiofrequency (including Zigbee technology, Bluetooth, etc.) and Wi-Fi, as well as similar elements.

12 Claims, 4 Drawing Sheets

(51) Int. Cl.
  *A41D 1/00*    (2018.01)
  *A61B 5/00*    (2006.01)
  *G06F 3/01*    (2006.01)
  *H05K 1/03*    (2006.01)
  *H05K 1/11*    (2006.01)
  *H05K 1/18*    (2006.01)
  *H05K 1/02*    (2006.01)

(52) U.S. Cl.
  CPC .............. *G06F 3/015* (2013.01); *H05K 1/038* (2013.01); *H05K 1/115* (2013.01); *H05K 1/18* (2013.01); *H05K 1/0283* (2013.01); *H05K 1/118* (2013.01); *H05K 2201/0281* (2013.01); *H05K 2201/10053* (2013.01)

(58) Field of Classification Search
  USPC ........ 361/757, 502, 525; 600/382, 388, 389, 600/390, 393, 484, 509, 529, 534; 439/8, 439/37; 442/181, 208, 316
  See application file for complete search history.

(56) References Cited

U.S. PATENT DOCUMENTS

| | | | |
|---|---|---|---|
| 6,233,135 B1* | 5/2001 | Farahmandi | H01G 9/038 361/502 |
| 6,350,129 B1* | 2/2002 | Gorlick | H01R 4/48 439/37 |
| 6,381,482 B1* | 4/2002 | Jayaraman | A61B 5/6805 600/388 |
| 6,687,523 B1* | 2/2004 | Jayaramen | A41D 13/1281 600/388 |
| 2003/0212319 A1* | 11/2003 | Magill | A61B 5/0408 600/382 |
| 2004/0009729 A1* | 1/2004 | Hill | D02G 3/441 442/208 |
| 2004/0009731 A1* | 1/2004 | Rabinowicz | A41D 13/1236 442/316 |
| 2005/0054941 A1* | 3/2005 | Ting | A61B 5/0408 600/529 |
| 2007/0038057 A1* | 2/2007 | Nam | A61B 5/04085 600/388 |
| 2007/0083096 A1* | 4/2007 | Paradiso | A61B 5/0408 600/388 |
| 2008/0015454 A1* | 1/2008 | Gal | A41D 13/1281 600/509 |
| 2008/0083721 A1* | 4/2008 | Kaiserman | A43B 3/0005 219/211 |
| 2008/0091097 A1* | 4/2008 | Linti | A41D 13/1281 600/389 |
| 2008/0143080 A1* | 6/2008 | Burr | D04B 1/14 280/495 |
| 2009/0012408 A1* | 1/2009 | Nagata | A61B 5/04085 600/484 |
| 2009/0272197 A1* | 11/2009 | Ridao Granado | G01L 1/20 73/828 |
| 2010/0185076 A1* | 7/2010 | Jeong | A61B 5/0408 600/388 |
| 2010/0185259 A1* | 7/2010 | Shiba | A61H 39/002 607/48 |
| 2010/0198043 A1* | 8/2010 | Holzer | A41D 13/1281 600/388 |
| 2010/0234715 A1* | 9/2010 | Shin | A61B 5/0402 600/388 |
| 2010/0286546 A1* | 11/2010 | Tobola | A61B 5/0816 600/534 |
| 2012/0136231 A1 | 5/2012 | Markel | |
| 2013/0075802 A1 | 3/2013 | Chen et al. | |
| 2013/0224551 A1 | 8/2013 | Hiralal et al. | |

OTHER PUBLICATIONS

Machine translation of KR20130081765 to Roh et al.
Machine translation of Abstract of TW201320310 to Chen et al.

\* cited by examiner

Figure 1A
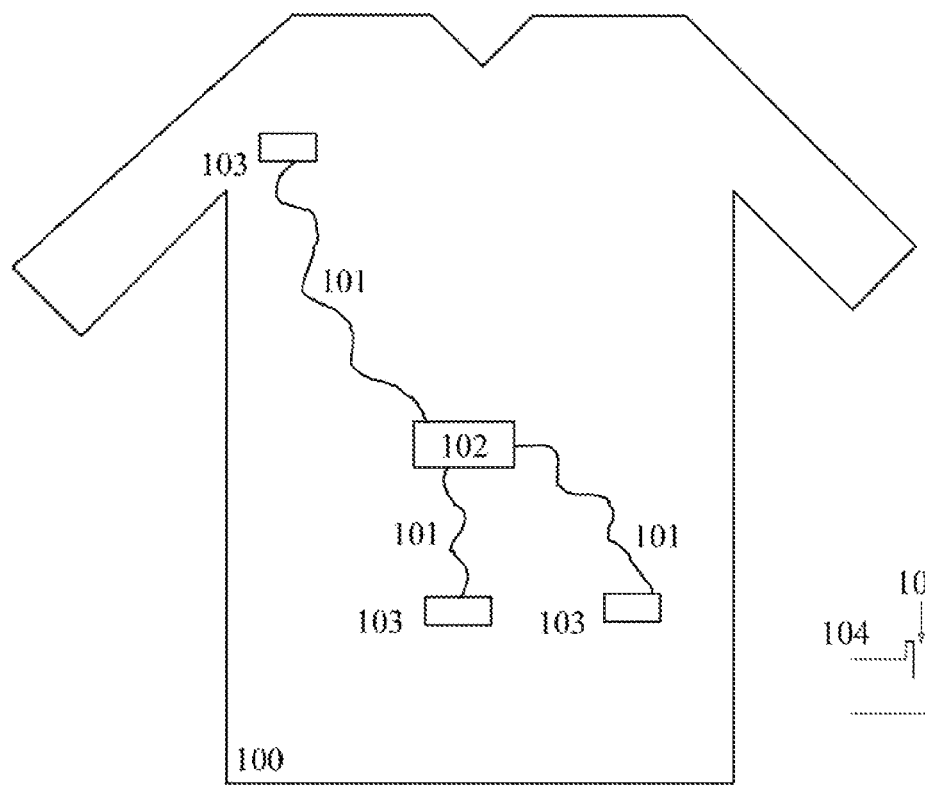
Figure 1B
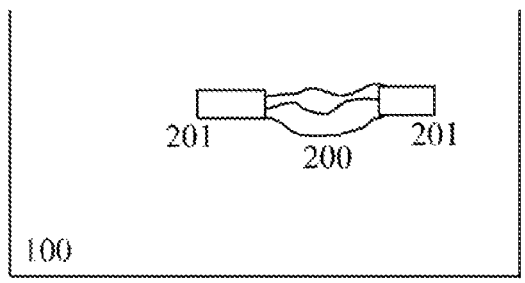
Figure 2A
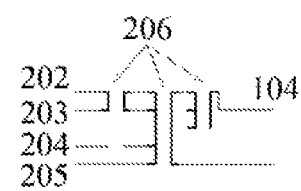
Figure 2B

TEXTILE MOTHERBOARD, HAVING A MODULAR AND INTERCHANGEABLE DESIGN, FOR MONITORING, REPORTING AND CONTROLLING

FIELD OF THE DISCLOSURE

The present disclosure relates to exemplary embodiments of a textile motherboard arrangement, and more particularly to textile motherboards that may be employed in garments, blankets, towels, tablecloths, gowns, etc., with non exclusive applicability to the medical, commercial, family-care, or sports fields.

MAIN OBJECTIVE OF THE INVENTION

A main object of the present invention is to render intelligent textiles that may be worn or utilized by users with the end goal of monitoring, informing, or controlling parameters of interest.

The textiles are rendered intelligent by incorporating into them at least one textile motherboard TMB, which can function with analog- and/or digital-electric and/or photonic signals. Furthermore, at least one central processing unit CPU or at least one peripheral may be connected to the TMB, in order to provide one of the abovementioned features to the intelligent textile. In order to bestow flexibility, the TMB design is modular; furthermore, both CPU and peripherals may be utilized interchangeably.

In a first exemplary arrangement of the TMB including CPU and peripherals, the intelligent textile may be able to perform monitoring. For instance, an intelligent textile with a TMB may be capable of monitoring user parameters such as temperature, the selection from a menu of options, solar exposure, pulse, etc.

In another exemplary embodiment of the TMB including CPU and peripherals, the intelligent textile may enable the person wearing it to inform her about events. For instance, an intelligent textile with a TMB may be able to inform the person wearing it about the presence of humidity by means of visual, vibrating, and audible alarms. Furthermore, an intelligent textile with a TMB may inform a portable device, such as a tablet or a smartphone, about further events of the person wearing it, for example during sports events.

Finally, in yet another exemplary arrangement of the TMB including CPU and peripherals designed to control, the intelligent textile may serve as a platform to manipulate various objects of interest. For example, an intelligent textile with a TMB may be able to control the call for assistance to a third person, after e.g. selecting a menu of options; additionally, a comparable embodiment may enable to control the lights of a public establishment.

BACKGROUND INFORMATION

There exist garments with three electrodes to monitor physiological parameters, such as the arrangement disclosed in the document US 2007/0078324 A1, and granted to Ravindra Wijisiriwardana in Apr. 5, 2007, which consists of a system or a garment that comprises at least three electrodes to monitor at least one physiological event of the person wearing it. Specially, one electrode is utilized to send an inverted noise signal as a feedback mechanism to eliminate the noise generated in the detection process. This system is particularly designed to measure the electrical characteristics of the user, such as cardiograms or cardiac frequency.

Another example of a comparable device is depicted in the document U.S. Pat. No. 8,340,740 B2 granted to Christian Holzer, Thorsten Habel, and Martin Gierich the 25 Dec. 2012, which consists of a garment that enables physiological monitoring. The measuring sensors are integrated into the garment. The device that monitors the physiological properties is located on the back of the garment, and may be integrated and fixed to the garment. It may also be detached from the garment.

A further instance of this type of devices is described in document US 2003/0212319 A1 granted to Alan Remy Magill on the 13 Nov. 2003, which consists of a physiological monitoring garment. In this approach the electricity is conducted by means of fibers from the skin surface to a garment that has a microprocessor, telemetry system, and power supply to monitor and transmit electrocardiogram data. The garment with the microprocessor may be detached, thus enabling the cleaning of the garment in contact with the skin. The system may also be used in reverse order, in order to provide electrical stimulation to the body.

Another example of these types of devices is shown in the document US 2012/0136231 A1 granted to Gal Markel on the 31 May 2012, which consists of a garment that provides physiological and environmental monitoring, as well as location information. This proposal is conformed of a garment or system of garments with the capacity to monitor health. The garment comprises a variety of electrocardiogram sensors, other sensors to monitor health, a processor, conductive fibers, as well as a communication unit in order to send physiological, environmental, and location data.

A final instance of this kind of devices is described in the document WO 2011/131235 A1 granted to Javier Guillen Arredondo and Sergio Guillen Barrionuevo the 27 Oct. 2011, which consists of a monitoring system. This proposal is composed of a monitoring system with one or more sensors adapted to measure one or more parameters, indicative of the physical health of the user. The proposal also includes a system to collect the data and an evaluation system to compare the values with predetermined information. At least one of the sensors is incorporated into a garment.

TECHNICAL PROBLEM TO SOLVE

Despite the fact that garments exist to monitor physiological parameters, the approaches known in the state-of-the-art do not have a textile motherboard scheme incorporated into the design of the devices.

Moreover even though some devices are detachable, they are not modular and none describe the feature of being interchangeable. For instance, once the device is designed to monitor cardiac frequency, that same design is not able to monitor another parameter, such as temperature.

Also absent in the state-of-the-art is the ability of the textiles to manipulate objects of interest, such as the lights of a public establishment, after selecting a (textile) menu of options.

BRIEF DESCRIPTION OF THE INVENTION

In order to address the abovementioned problem in the state-of-the-art, it is the object of the present invention to disclose embodiments that provide the structure of a textile motherboard (TMB) The substrate of the TMB, object of the present invention, is conformed of textile material. Furthermore, the TMB may be structured with single-layer or multiple-layer designs, incorporating perforations for layer interconnection. Layers and perforations are conformed of textile materials and are incorporated into the TMB by means of textile manipulation techniques.

The routing of the TMB includes at least two different types of routing: maze routing and X-Y routing. Both routing types may be implemented in the TMB, for instance by utilizing textile printing techniques or by incorporating the routes by following a required pattern using textile manipulation techniques.

The peripherals may be broadly classified as input or output peripherals. In order to yield flexibility, the TMB incorporates terminals in the CPU and peripherals that simplify the modular and interchangeable design of the TMB by employing conventional textile connectors.

Finally, the implementation of an interchangeable TMB design, including input and output peripherals, enables the user to manipulate objects of interest, such as the lights of a public establishment, after selecting a menu of options.

BRIEF DESCRIPTION OF DRAWINGS

FIG. 1A.—Shows a design of a plausible embodiment of a single-layer textile motherboard (TMB);

FIG. 1B.—Depicts the cross section of a plausible embodiment of a multiple-layer textile motherboard wherein the use of "VIAs" for the interconnection between the multiple layers is highlighted;

FIG. 2A.—Illustrates the utilization of textile materials to conform a TMB, such as the embodiment depicted in FIG. 1A;

FIG. 2B.—Shows the cross section of an embodiment of a multiple-layer textile motherboard wherein the layers are incorporated into the front- and back-parts of the textile, and are isolated in the middle part;

DETAILED DESCRIPTION OF THE INVENTION

Figure 2C:
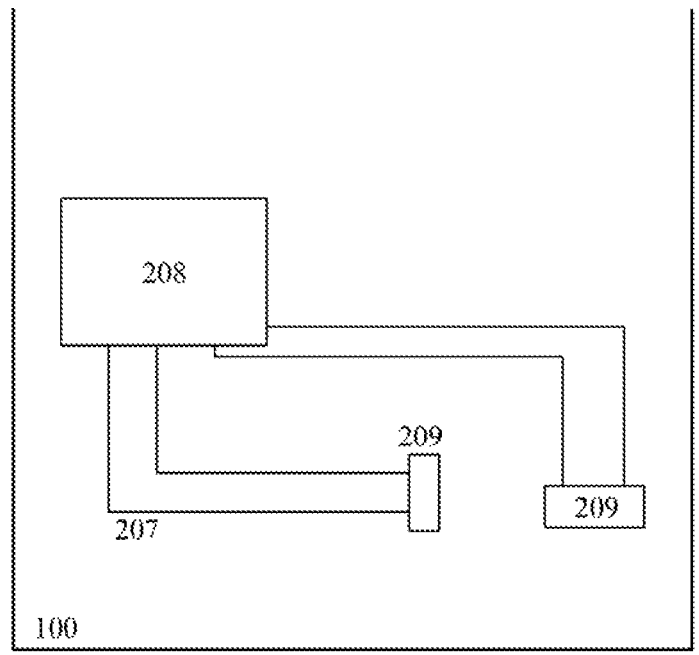
FIG. 2C.—Depicts the implementation of X-Y routing in a textile garment, assuming that the routing is performed on the top layer of the motherboard.

The present disclosure relates to an apparatus that may be employed in garments, blankets, towels, tablecloths, gowns, etc., which may consist of a first element (100), a second element (200), a third element (300), a fourth element (400) and a fifth element (500).

The first element (100) consists of a textile motherboard (100), TMB. The design of the TMB is modular and permits to interchange elements within the TMB. The TMB utilizes connectors to incorporate exemplary components such as central processing units (102) or peripherals (103).

An exemplary embodiment of the present disclosure of the TMB (100) is depicted in FIG. 1A. According to this exemplary embodiment, the TMB (100) consists of at least one substrate layer, with at least one conductive routing (101), and at least one terminal connected to the at least one conductive routing wherein exemplary components, such as a CPU (102) or a peripheral (103) or a combination thereof, may be installed. The TMB (100) defines an electronic or a photonic circuit, which is a function of the arrangement of peripherals (103) and CPU (102) utilized, wherewith information may be monitored, manipulated, as well as emitted with the object of signalizing, or informing, or controlling depending on the intended purpose of the product that incorporates the TMB.

In FIG. 1B, an exemplary embodiment of the TMB is shown to exhibit a multiple-layer structure (104) in addition to perforations for the interconnection between layers (109, 110, 111); known as Vertical Interconnect Accesses or "VIAs" to those skilled in the art.

A first exemplary layer (105) may serve as a platform to guide a first digital or analog signal. A second exemplary layer (106) may serve as a platform to guide a second digital or analog signal. A third exemplary layer (107) may serve as a platform to provide a constant electric or photonic signal. A fourth exemplary layer (108) may serve as a platform to provide a reference. The foregoing descriptions of the third and fourth exemplary layers could for instance provide +5V and 0V signals, respectively. The aforementioned layers may be employed repetitively, as deemed necessary by a design. This layer structure is illustrative and does not limit the embodiments of a particular TMB.

According to the exemplary embodiment of the present disclosure shown in FIG. 1B, layer interconnection ensues by utilizing perforations (109, 110, 111) or Vertical Interconnect Accesses, known as "VIAs" to those skilled in the art. A first exemplary VIA that can be employed is the tag VIA (109). A second exemplary VIA that may be utilized is the thru VIA (110). A third exemplary VIA that can be used is the sequential VIA (111). Additional exemplary VIAs that may be employed include photo-defined, controlled depth, or buried VIAs. This list of VIAs is illustrative and does not limit the embodiments of a particular TMB.

The second element (200) consists of textile material with the capacity to transmit and isolate digital- and/or analog-electric and/or photonic signals, or a combination thereof. In FIG. 2A an exemplary embodiment of a TMB substrate, which is conformed of textile material, is depicted. In such exemplary substrate (100), routing structures (200) may be incorporated to guide signals to and from components (201).

The routing structures (200) within the TMB (100) may consist of electric textile conductors, a textile arrangement that incorporates fiber optics or waveguides, as well as printed or stamped textiles with the conductive routing.

An exemplary TMB may consist of knitted or weaved textiles, such as those known in the art, which define a substrate layer (100), and wherein conductive textiles (200) may be intercalated appropriately, in order to define the intended routings for the circuit. Exemplary conductive textiles (200) may extend from a terminal up to a CPU (201) or may exhibit a desired extension for a specific function, thus defining a determined conductive routing.

According to the exemplary embodiment of the present disclosure shown in FIG. 2B, a TMB may implement multiple textile structures, such as knitted or weaved textiles, as well as stampings or printings that serve as layers (104), and that define independent conductive routings (202, 203, 204, 205), wherein isolating layers may be superposed in order to avoid interference between routings, and wherein the interconnection between the different conductive routings may be done by means of textile VIAs (206)

According to one exemplary embodiment of the present disclosure, a TMB may incorporate a substrate layer (100) that simultaneously functions as an isolating layer. Moreover, the configuration of knitted or weaved textiles, stampings, or printings (200), which define the conductive routings, may be placed adjacent one to the other in a single plane, separated by isolating layers. According to still another exemplary embodiment of the TMB, a configuration of knitted or weaved textiles, stampings, or printings (104), which define the conductive routings, may be placed superposed (202, 203, 204, 205) in an alternating manner with isolating layers.

Exemplary interconnections between knitted or weaved textiles localized in a single layer can be implemented by employing other knitted or weaved textiles, which define the aforementioned exemplary interconnections. Exemplary interconnections between printings localized in a single layer can be implemented by employing other printings, which define the aforementioned exemplary interconnections. Exemplary interconnections between stampings localized in a single layer can be implemented by employing other stampings, which define the aforementioned exemplary interconnections.

Exemplary interconnections between knitted or weaved textiles localized in multiple layers can be implemented by employing other knitted or weaved textiles, which define the aforementioned exemplary interconnections. Exemplary interconnections between printings localized in multiple layers can be implemented by employing other printings, which define the aforementioned exemplary interconnections. Exemplary interconnections between stampings localized in multiple layers can be implemented by employing other stampings, which define the aforementioned exemplary interconnections.

Exemplary interconnections between textiles localized in multiple layers can be implemented by using textile VIAs between the corresponding textiles. Exemplary interconnections between printings localized in multiple layers can be implemented by using textile VIAs between the corresponding printings. Exemplary interconnections between stampings localized in multiple layers can be implemented by using textile VIAs between the corresponding stampings.

The exemplary conductive routings (200), layers (202, 203, 204, 205), and VIAs (206) are conformed of textile material and are implemented by employing textile manipulation techniques. A first layer (202) may be incorporated into the front section of a textile. A second layer (203) and a third layer (204) may be isolated. A fourth layer (205) may be incorporated into the back section of a textile. Moreover, each of the first (202), second (203), third (204), and fourth (205) layers may be conformed by utilizing individual textiles.

The exemplary conductive routings (200), layers (202, 203, 204, 205), and VIAs (206) of a TMB (100) may be implemented by employing known textile manipulation techniques such as knitting, weaving, stamping, perforating, or may also be printed on the textiles.

The exemplary embodiment of the present disclosure shown in FIG. 2C depicts the routing of a TMB (100). The routing of a TMB (100) includes at least two different types of routings: maze routing and X-Y routing (207). Both routing types may be implemented in a TMB (100), for instance by utilizing textile printing techniques or by incorporating the routes by following a required pattern using textile manipulation techniques. The routing guides the signals between the CPU (208) and a means to register information (209) or between the CPU and the combination of peripherals (209).

Figure 3:
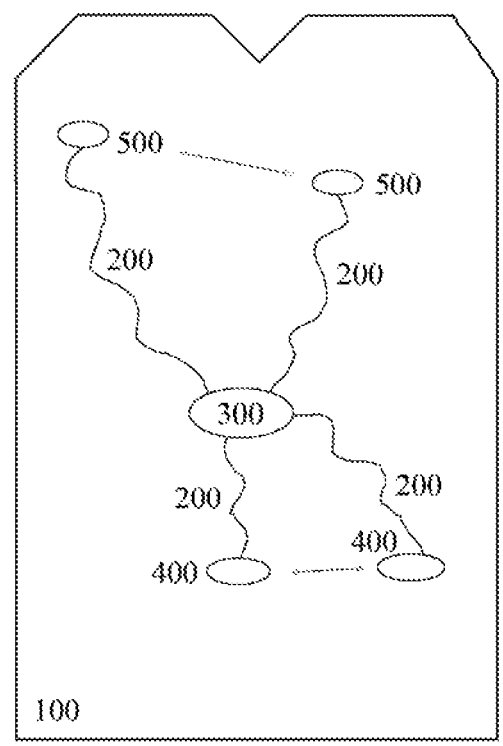
FIG. 3.—Shows a layout embodiment of an intelligent vest with exchangeable input and output devices.

The third element (300), fourth element (400), and fifth element (500) consist of a CPU (300), input peripherals (400), and output peripherals (500) connected to a TMB (100), Which are shown in an exemplary embodiment in FIG. 3. Such exemplary embodiment of a TMB (100) may be characterized by allowing the interchange of CPU (300) or peripheral elements (400, 500), in order to monitor different variables, signalize, inform, or control. In this exemplary embodiment, TMB (100), routing (200), CPU (300), and peripherals (400, 500) are washable.

Exemplary CPU (300) and peripherals (400, 500) may be mounted on textile boards, as well as rigid or flexible printed circuit boards PCBs. Each exemplary board may incorporate discrete electronic elements (such as resistors, integrated circuits, capacitors, etc.) or discrete photonic elements (such as Bragg gratings, beam dividers, interferometers, etc.)

An exemplary CPU (300) may consist of a photonic or an electronic device that processes signals sent by the peripheral elements, and sends information by employing appropriate peripheral elements. Exemplary CPUs (300) may include a microcontroller or a microprocessor or a comparable element.

The CPU (300) connects with the peripherals (400, 500) employing the textile routing (200). The TMB (100) peripherals (400, 500) may be broadly classified as input (400) and output (500) devices.

Exemplary input peripherals (400) consist of elements such as photonic transducers or electronic transducers or combinations thereof. Therefore, exemplary input peripherals (400) may include capacitive sensors or temperature sensors or accelerometers or respiratory frequency sensors or humidity sensors or magnetometers or chest expansion sensors or gyroscopes or pulse sensors or muscular activity sensors or similar devices.

Exemplary output peripherals (500) may include elements like a screen or a vibration device or an audible device or an illuminating device or a device capable of emitting information or a memory module or a serial communications module or a radio frequency communications module (using Zigbee technology, Bluetooth, etc.) or a "Wi-Fi" communications module or similar devices.

Figure 4:
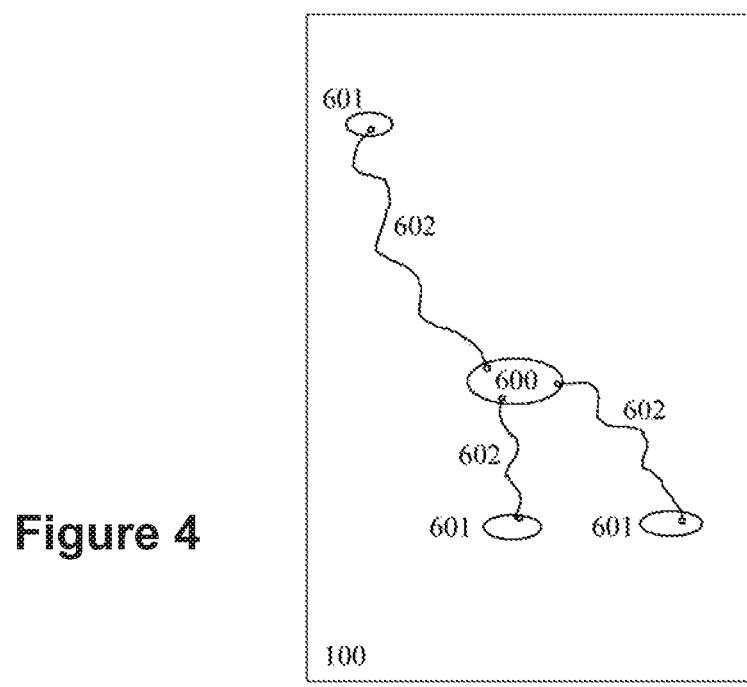
FIG. 4.—Illustrates the employment of conventional textile connectors that facilitate the modular and exchangeable design.

In order to yield flexibility, the TMB (100) incorporates terminals, in the CPU (600) and peripherals (601), which simplify the modular and interchangeable design by employing conventional textile connectors such as snaps, hooks and eyes, hooks and loops (Velcro), or similar elements. This aspect of the invention is illustrated in the exemplary embodiment of FIG. 4. Furthermore, the exemplary terminals exhibit appropriate characteristics in order to be able to interchange the CPU (600) or the peripheral elements (601) to monitor different variables, signalize, inform, or control.

Each terminal is adhered to a determined routing, by using textile manipulation techniques, which enables the conduction of signals between elements of a TMB. For instance, an exemplary terminal in the form of a snap (601) may be sewed to the corresponding routing (602) to facilitate the communication between a peripheral (601) and a CPU (600).

Figure 5:
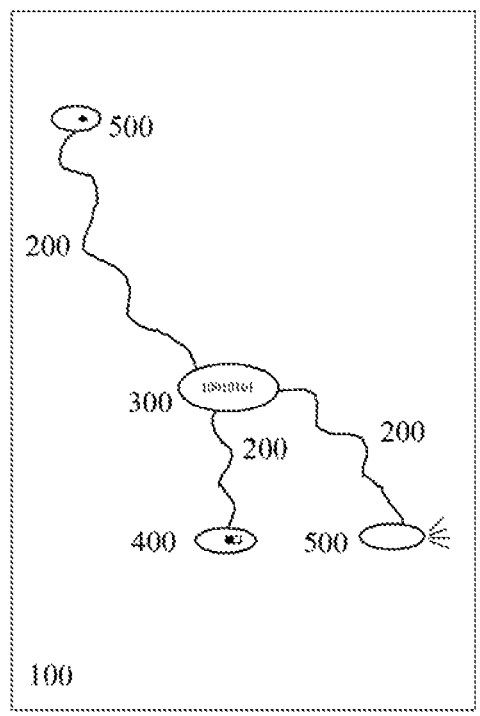
FIG. 5.—Depicts an embodiment in the form of an intelligent tablecloth, which enables the user to manipulate objects of interest, such as the lights of a public establishment, after selecting a (textile) menu of options.

A final exemplary embodiment of the present disclosure, shown in FIG. 5, depicts a TMB (100), including routing (200), CPU (300), input (400), and output (500) peripherals to enable a user to manipulate objects of interest, such as the lights of a public establishment, after selecting a (textile) menu of options.

The foregoing merely illustrates the principles of the disclosure. Various modifications and alterations to the described embodiments will be apparent to those skilled in the art in view of the teachings herein.

Preferred Approaches to Implement the Invention

By utilizing a TMB conformed of specific CPU and peripherals, a garment may be able to monitor, inform, and control. For instance, an intelligent textile in the form of a gown with a peripheral, periodically scanned by a CPU, may be utilized to monitor temperature and inform about the presence/absence of fever, and may control with a button the call for assistance. Moreover, due to the modular and interchangeable design, the input peripheral may, for instance, be changed from a temperature detector to a pulse detector.

By employing a determined arrangement of TMB, CPU, and peripherals, an intelligent textile may enable the person wearing it to inform her about events. For instance, an intelligent textile may be able to inform about the presence of humidity by means of visual, vibrating, and audible alarms. Furthermore, an intelligent textile may be capable of informing a portable device, such as a tablet or a smartphone, about further events of the person wearing it, for example during sports events.

Finally, by implementing a specific arrangement of TMB, CPU, and peripherals designed to control, an intelligent textile may serve as a platform to manipulate various objects of interest. For example, an intelligent textile may be able to control the call for assistance to a third person, after selecting a menu of options; as well as enabling the control of lights of a public establishment.

The invention claimed is:

1. A textile motherboard, characterized by the implementation of:
   at least one substrate that consists of a textile material and serves as support for a textile circuit or part of it; wherein the textile substrate additionally includes at least one portion of a textile conductive layer and a portion of a textile isolating layer;
   at least a conductive routing that defines trajectories of the textile circuit or part of it, in the at least one portion of textile conductive layer, and that serves as transmission platform for the textile circuit that conforms the textile motherboard;
   at least one textile component incorporated into the substrate and attached to the conductive routing, which conforms a peripheral of, the textile motherboard, or that conforms a peripheral or a part of a peripheral employable in another textile motherboard;
   at least an interconnection terminal attached to the conductive routing, which consists of at least a means of textile union, which enables the connection and disconnection of at least one textile, electronic, or photonic peripheral, which exhibits at least one complementary means of textile union, which enables the interchange of peripherals usable in the textile motherboard;
   wherein the at least one conductive routing is attached by means of textile vertical interconnect accesses (VIA) to another conductive routing placed in another portion of conductive layer in the at least one substrate and;
   the textile motherboard is configured to monitor, inform, and control parameters of a user that wears a garment or utilizes an article, which incorporates such textile motherboard.

2. Textile motherboard according to claim 1, wherein the textile motherboard is conformed of at least two substrates and at least one conductive routing in each substrate, and the connection between conductive routings is achieved by means of textile vertical interconnect accesses (VIA).

3. Textile motherboard according to claim 1, wherein the textile vertical interconnect accesses (VIA) may be selected from a tag or a sequential or a thru or a photo-defined or a controlled depth or a buried VIA, and alike structures, or combinations thereof.

4. Textile motherboard according to claim 1, wherein the substrates or portions of conductive layers are separated by at least one isolating layer.

5. Textile motherboard according to claim 4, wherein the isolating layer may be the same as the substrate layer.

6. Textile motherboard according to claim 1, wherein one of the at least one textile, electronic, or photonic peripheral includes a central processing unit (CPU).

7. Textile motherboard according to claim 6, wherein the central processing unit (CPU) consists of a microcontroller or a microprocessor or a comparable element.

8. Textile motherboard according to claim 1, wherein the at least one conductive routing consists of a textile electric conductor or a textile arrangement that incorporates a fiber optic or a textile arrangement that incorporates a waveguide.

9. Textile motherboard according to claim 8, wherein the textile conductor consists of an interwoven route within the textile that conforms the substrate layer.

10. Textile motherboard according to claim 8, wherein the textile conductor consists of multiple layers, which define the conductive routings, and are placed adjacent in a single plane separated by isolating layers, or are placed superposed in an alternating manner with the isolating layers.

11. Textile motherboard according to claim 1, wherein the interconnection terminal is configured to enable the interchange of central processing units or of peripheral elements, in order to monitor different variables or to inform or to signalize or to control operations of alike elements.

12. Textile motherboard according to claim 11, wherein the interconnection terminal consists of a snap or a hook or a hook and loop system or a similar element attached to the conductive routing.

* * * * *